US012611297B2

(12) United States Patent
Wang et al.

(10) Patent No.: US 12,611,297 B2
(45) Date of Patent: Apr. 28, 2026

(54) MULTIFOCAL LENS

(71) Applicant: HOYA Medical Singapore Pte. Ltd., Singapore (SG)

(72) Inventors: Jun Wang, Singapore (SG); Alexey Simonov, Singapore (SG)

(73) Assignee: HOYA Medical Singapore Pte. Ltd., Singapore (SG)

( * ) Notice: Subject to any disclaimer, the term of this patent is extended or adjusted under 35 U.S.C. 154(b) by 664 days.

(21) Appl. No.: 18/016,311

(22) PCT Filed: Jul. 15, 2021

(86) PCT No.: PCT/JP2021/027614
§ 371 (c)(1),
(2) Date: Jan. 13, 2023

(87) PCT Pub. No.: WO2022/014723
PCT Pub. Date: Jan. 20, 2022

(65) Prior Publication Data
US 2023/0301774 A1 Sep. 28, 2023

(30) Foreign Application Priority Data

Jul. 15, 2020 (EP) ..................................... 20186025

(51) Int. Cl.
*A61F 2/16* (2006.01)
(52) U.S. Cl.
CPC ............ *A61F 2/1618* (2013.01); *A61F 2/164* (2015.04); *A61F 2/1656* (2013.01)
(58) Field of Classification Search
CPC .................................................... A61F 2/1654
See application file for complete search history.

(56) References Cited

U.S. PATENT DOCUMENTS

| | | | |
|---|---|---|---|
| 2007/0258143 A1 | 11/2007 | Portney | |
| 2012/0283825 A1 | 11/2012 | Houbrechts et al. | |

(Continued)

FOREIGN PATENT DOCUMENTS

| | | |
|---|---|---|
| CN | 101495908 A | 7/2009 |
| EP | 377 493 A1 | 10/2011 |

(Continued)

OTHER PUBLICATIONS

International Search Report dated Nov. 18, 2021, for corresponding International Application No. PCT/JP2021/027614 filed Jul. 15, 2021; total pp. 5.

(Continued)

*Primary Examiner* — Javier G Blanco
(74) *Attorney, Agent, or Firm* — Snell & Wilmer L.L.P.

(57) ABSTRACT

The invention relates to a multifocal lens 1 having several concentric diffractive zones 7, 8, 9, 10 on a lens surface 2, wherein in each diffractive zone a diffraction phase structure is defined, which is expressible by the following function or by a smoothed version of the function:

$$\phi(\xi) = 2\pi \times \begin{cases} p_1\xi, & 0 \leq \xi < w_1 \\ p_2\xi + q_2, & w_1 \leq \xi < w_2, \\ p_3\xi + q_3, & w_2 \leq \xi < 1 \end{cases}$$

wherein $\xi$ indicates a position within the respective diffractive zone in a radial direction, $\phi(\xi)$ indicates a phase shift experienced by light passing through the position indicated by $\xi$, $w_1$ and $w_2$ define a spatial partitioning of the respective diffractive zone in the radial direction, $p_1$, $p_2$ and $p_3$ indicate gradients and $q_2$ and $q_3$ are constants. The position $\xi$ depends quadratically on a radial distance to the center of the lens (Continued)

surface and is normalized with respect to the radial width of the respective diffractive zone and the gradients $p_1$, $p_2$ and $p_3$ are negative.

18 Claims, 9 Drawing Sheets

(56)                    References Cited

U.S. PATENT DOCUMENTS

| 2018/0147050 A1 | 5/2018 | Choi et al. |
| 2019/0254810 A1 | 8/2019 | Tiwari et al. |
| 2019/0339545 A1 | 11/2019 | Schwiegerling |

FOREIGN PATENT DOCUMENTS

| EP | 375 276 | B1 | 5/2016 |
| EP | 130 314 | A1 | 2/2017 |
| JP | 2010158315 | A | 7/2010 |
| JP | 2016189026 | A | 11/2016 |
| JP | 201888247 | A | 6/2018 |
| JP | 2018525199 | A | 9/2018 |
| JP | 2019220163 | A | 12/2019 |
| WO | 2013118177 | A1 | 8/2013 |

OTHER PUBLICATIONS

Written Opinion of the International Searching Authority dated Nov. 18, 2021, for correspondence International Application No. PCT/JP2021/027614 filed Jul. 15, 2021; total pp. 6.

O'shea Donald C. et al.: "Diffractive Optics : Design, Fabrication, and Test" In: "Diffractive Optics", Jan. 1, 2003 (Jan. 1, 2003), SPIE, 1000 20th Street, Bellingham, WA 98227-0010 USA, XP093204505, ISBN: 978-0-8194-5171-2, pp. 57-82.

International Preliminary Report on Patentability dated Jan. 17, 2023, for corresponding International Application No. PCT/JP2021/027614 filed Jul. 15, 2021; total pp. 7.

Notification of the First Office Action dated Feb. 4, 2026 and Search Report dated Feb. 2, 2026 in corresponding Chines Patent Application No. 202180062701.6 filed Jul. 15, 2021; total 11 pages.

MULTIFOCAL LENS

CROSS-REFERENCE TO RELATED APPLICATIONS

The present application is a U.S. National Stage entry under 35 U.S.C. § 371 of International Application No. PCT/JP2021/027614 filed Jul. 15, 2021, which claims priority to, and the benefit of European Application No. 20186025.1 filed Jul. 15, 2020, which applications are hereby incorporated by reference in their entirety.

FIELD OF THE INVENTION

The invention relates to a multifocal lens having several concentric diffractive zones on a surface of the lens. The invention relates further to a method for producing a multifocal lens having several concentric diffractive zones on a surface of the lens and to a multifocal lens being producible by this method.

BACKGROUND OF THE INVENTION

The European patent EP 2 375 276 B1 discloses a diffractive multifocal lens having an annular diffraction pattern for exhibiting a light diffraction effect, which is formed concentrically repeatedly on a surface of the lens. Although the diffractive multifocal lens disclosed in the European patent already provides good optical properties, a further improvement of the optical properties is desired, for instance, with respect to chromatic aberration, visual acuities for certain vision distances, et cetera.

SUMMARY OF THE INVENTION

It is an object of the present invention to provide a multifocal lens having several concentric diffractive zones on a surface of the lens, which has improved optical properties.

In a first aspect of the present invention a multifocal lens having several concentric diffractive zones on a surface of the lens is presented, wherein in each diffractive zone a diffraction phase structure is defined, which is expressible by the following piecewise function, which comprises three phase terms, or by a smoothed version of the following piecewise function:

$$\phi(\xi) = 2\pi \times \begin{cases} p_1\xi, & 0 \le \xi < w_1 \\ p_2\xi + q_2, & w_1 \le \xi < w_2, \\ p_3\xi + q_3, & w_2 \le \xi < 1 \end{cases} \quad (1)$$

wherein $\xi$ indicates a position within the respective diffractive zone in a radial direction, $\phi(\xi)$ indicates a phase shift experienced by light passing through the position indicated by $\xi$, $w_1$ and $w_2$ define a spatial partitioning of the respective diffractive zone in the radial direction in accordance with the three phase terms, $p_1$, $p_2$ and $p_3$ indicate gradients of the three phase terms and $q_2$ and $q_3$ are constants, wherein $\xi$ depends quadratically on a radial distance to the center of the surface of the lens and is normalized with respect to the radial width of the respective diffractive zone and wherein the gradients $p_1$, $p_2$ and $p_3$ are negative.

It has been found that a multifocal lens having several concentric diffractive zones on a surface of the lens, wherein in each diffractive zone a diffraction phase structure is defined, which is expressible by the piecewise function in accordance with equation (1), wherein the parameter depends quadratically on the radial distance to the center of the surface of the lens and is normalized with respect to the radial width of the respective diffractive zone and wherein the gradients $p_1$, $p_2$ and $p_3$ are negative, allows for improved optical properties like reduced chromatic aberration, high visual acuities at certain vision distances, et cetera. In particular, the lens can lead to a reduction of potential dysphotopsia effects under mesopic and scotopic illumination conditions, particularly when the pupil is large. Moreover, the smoothing of the phase shift function $\phi(\xi)$ can improve the machinability of the diffraction phase structure and can decrease unwanted light scattering effects which might be caused by sharp transition regions on the diffractive surface. The phase shift preferentially refers to a design wavelength of the light of 546 nm and incoming light propagating parallel to the optical axis of the lens.

The radial distance to the center of the surface of the lens, i.e. the radial position, or radius, of a point on the lens surface, is preferably given in terms of a distance to a central axis of the lens, measured perpendicularly to the central axis, wherein the central axis may be an axis of rotational symmetry of the lens surface. In principle, however, the radial distance to the center of the surface of the lens may also be measured along the lens surface. If the lens surface is flat, i.e. not curved, the two options of measuring the radial position of a point on the lens surface coincide.

The concentric diffractive zones are preferentially annular zones, wherein the innermost annular diffractive zone preferentially surrounds the center of the lens surface which of course is infinitesimally small and which could therefore also be regarded as being substantially a circular zone on the lens surface.

The lens is preferentially a trifocal lens with diffractive orders 0, +1 and +2. Due to the provision of three foci, the focal range can be relatively large, in comparison to monofocal and bifocal lenses. This may have the effect that a person does not need any additional glasses for certain daily activities. Moreover, the use of the three diffractive orders 0, +1, +2, specifically, allows to further minimize chromatic aberration of the eye, thus further mitigating a potential risk of chromatic visual disturbances.

The parameters of the function $\phi(\xi)$ may satisfy at least one of the conditions $w_1=1-w_2$, $p_1=p_3$, $p_1{}^*p_2$, $p_3 \# p_2$, and $p_1$, $p_2$, $p_3 < 0$. In particular, the parameters might satisfy a combination of the conditions, especially all of these conditions.

The variable $\xi$ on which the function $\phi(\xi)$ depends may be expressible as a linear function of the square of the radius, wherein the linear function is normalized with respect to a difference between the square of the radius at the outer boundary of the diffractive zone and the square of the radius at the inner boundary of the diffractive zone.

In an embodiment the constants $q_2$ and $q_3$ are positive. This is particularly the case for lenses of types which will below be named "far dominant" lens type and "near dominant" lens type. Since the constants $q_2$ and $q_3$ are positive, more than half of the diffractive profile sticks out from the refractive surface, which allows for further improved optical properties. In particular, in an embodiment the gradient $p_1$ is within a range from −1.1 to −1.0, the gradient $p_2$ is within a range from −1.1 to −1.0, the gradient $p_3$ is within a range from −1.1 to −1.0, the constant $q_2$ is within a range from 0.3 to 0.4 and the constant $q_3$ is within a range from 1.0 to 1.1. It may be defined that lenses having parameters in these ranges are lenses of the far dominant lens type. It has been found that these features lead to three foci for near, intermediate and far vision, wherein a relatively high far-focus contrast level and sufficiently high intermediate-focus and near-focus contrast levels are achieved. Thus, a very high visual acuity can be provided for far vision and still sufficiently high acuities can be provided for intermediate and near vision.

It is also possible that the gradient $p_1$ is within a range from −1.2 to −1.0, the gradient $p_2$ is within a range from −1.3 to −1.2, the gradient $p_3$ is within a range from −1.2 to −1.0, the constant $q_2$ is within a range from 0.7 to 0.8 and the constant $q_3$ is within a range from 1.0 to 1.2. It may be defined that lenses having parameters in these ranges are lenses of the near dominant lens type. It has been found that these features lead to three foci for near, intermediate and far vision, wherein a relatively high near-focus contrast level and sufficiently high intermediate-focus and far-focus contrast levels are achieved. Thus, a very high visual acuity can be provided for near vision and still sufficiently high acuities can be provided for intermediate and far vision.

Moreover, in an embodiment the gradient $p_1$ is within a range from −1.2 to −0.4, the gradient $p_2$ is within a range from −1.0 to −0.1, the gradient $p_3$ is within a range from −1.2 to −0.4, the constant $q_2$ is within a range from −0.2 to 0.3 and the constant $q_3$ is within a range from 0.4 to 1.2. It may be defined that lenses having parameters in these ranges are lenses of a lens type which might be named "intermediate vision" lens type. These features can provide an extended depth of focus at intermediate vision distance and can target to visual acuities with no dips from far distance to near add power distance. Moreover, these features can lead to an improved near-distance visual acuity and at the same time ensure good far-distance visual acuity.

Preferentially, the constant $w_1$ is 0.25 and the constant $w_2$ is 0.75 such that the radial width of the middle phase term is twice the radial width of the inner phase term and twice the radial width of the outer phase term. It has been found that also these specific values for the constants $w_1$ and $w_2$ lead to improved optical properties.

Preferentially, the radial width of the diffractive zones decreases with increasing radial distance of the respective diffractive zone to the center of the lens surface. Moreover, preferentially the surface of the lens, on which the diffractive zones are provided, is an anterior surface of the lens. It is further preferred that the diffractive zones extend over a central portion of the surface of the lens, wherein preferentially the outer border of the outermost diffractive zone has a radial distance to the center of the surface being equal to or smaller than 3.2 mm or equal to or smaller than 4.0 mm. In particular, for lenses of the far dominant and near dominant type, the radial distance to the center of the surface is equal to or smaller than 3.2 mm and, for lenses of the intermediate vision lens type, the radial distance to the center of the surface is equal to or smaller than 4.0 mm. It has been found that also these specific features lead to improved optical properties.

It is preferred that the surface, on which the several diffractive zones are provided, is a refractive surface of the lens such that the outermost diffractive zone is surrounded by a refractive zone which does not comprise a diffractive structure. Thus, the lens surface is preferentially a refractive surface, i.e. a curved surface, which provides a base refractive power. Preferentially, the lens comprises two refractive surfaces providing the base refractive power, wherein preferentially on one of these refractive surfaces the diffractive zones are provided. The lens therefore preferentially has a lens surface, wherein an inner area with the diffractive zones provides refractive and diffractive power and the outer area of the lens surface, which surrounds the inner area, provides refractive power only. The refractive property contributes to a far-focus light field. The use of the refractive surface improves the far-vision visual acuity. It is further preferred that the refractive surface is an aspheric lens surface. By using the aspheric lens surface the overall imaging performance can be further improved. In particular, the sensitivity of the eye to potential decentrations can be reduced. Moreover, aberrations of the eye can be corrected.

It is also preferred that the number of the diffractive zones is at least four. In particular, the number of diffractive zones might be exactly four. It has been found that by using four diffractive zones a reduction of potential dysphotopsia effects under mesopic and scotopic illumination conditions might be reduced, particularly when the pupil is large.

The lens is preferentially made of a lens material comprising an acrylic polymer. The lens material might further comprise an ultraviolet light absorbing agent like benzotriazole and/or a blue-light-filtering chromophore like monomethine. For more details regarding preferred lens materials reference is made to EP 2 375 276 B1 and U.S. Pat. No. 8,556,416 B2, which are herewith incorporated by reference.

The diffractive multifocal lens is preferentially an ocular lens, especially a contact lens or an intraocular lens. In particular, the lens is intended to be placed into the capsular bag of the eye after extracapsular cataract removal, functioning as a refractive and diffractive medium to replace the natural crystalline lens of the eye.

The smoothed version of the function $\phi(\xi)$ is preferentially obtained by convoluting the function $\phi(\xi)$ with a Gaussian kernel, wherein the Gaussian kernel preferentially has a standard deviation within a range from 0.02 to 0.04. In a preferred embodiment the standard deviation is 0.03. It has been found that such standard deviations lead to an optimized compromise between a) being relatively easily manufacturable and b) having very good optical properties.

In an embodiment the radial distance of the outer border of at least the innermost diffractive zone to the center of the surface of the lens, i.e. its radial position, is defined by $$r_k = \sqrt{\frac{2\lambda k}{p} + k^2 \lambda^2}, \tag{2}$$

wherein k indicates the respective diffractive zone, with k=1 indicating the innermost diffractive zone and k ascending in integer steps in outward direction, $\lambda$ is the wavelength of the light and p is a predefined value defining an add power. Preferentially $\lambda$ is the design wavelength of 546 nm. The value p for the add power might be, for instance, 1.75 D. In an embodiment, particularly if the lens is of the far dominant or near dominant lens type, the outer border of each diffractive zone is defined by this equation.

In an embodiment equation (2) defines the outer border of the innermost diffractive zone and the outer border of the other diffractive zones is defined by $$r_k = \left( r_{k-1}^2 + \lambda^2 + \sqrt{\frac{4\lambda^2}{p^2} + 4\lambda^2 r_{k-1}^2} \right)^{1/2}, \tag{3}$$

Particularly lenses of the intermediate vision lens type use equation (2) for the outer border of the innermost diffractive zone only and equation (3) for the outer borders of the further diffractive zones. It has been found that these outer borders can lead to further improved optical properties.

Preferentially, the constants $w_1$ and $w_2$ are the same for all diffractive zones. Moreover, in an embodiment the gradients $p_1$, $p_2$ and $p_3$, and the constants $q_2$ and $q_3$ are the same for all diffractive zones. This might especially be the case for a lens of the far dominant lens type or the near dominant type. In a further embodiment the gradients $p_1$, $p_2$ and $p_3$, and the constants $q_2$ and $q_3$ are not the same for all diffractive zones. This might especially be the case for a lens of the near dominant type or the intermediate vision lens type. In particular, the gradients $p_1$, $p_2$ and $p_3$, and the constants $q_2$ and $q_3$ of the innermost diffractive zone might differ from the gradients $p_1$, $p_2$ and $p_3$, and the constants $q_2$ and $q_3$ of the other diffractive zones. Also this might especially be the case for a lens of the near dominant type or the intermediate vision lens type. Moreover, in an embodiment the gradients $p_1$, $p_2$ and $p_3$, and the constants $q_2$ and $q_3$ of the other diffractive zones might be the same for all other diffractive zones. This might especially be the case for a lens of the near dominant type. Furthermore, in an embodiment the gradients $p_1$, $p_2$ and $p_3$, and the constants $q_2$ and $q_3$ are different for all diffractive zones. Thus, in an embodiment there are not two diffractive zones having the same parameters $p_1$, $p_2$, $p_3$, $q_2$ and $q_3$. This might especially be the case for a lens of the intermediate vision lens type. It has been found that this might lead to further improved optical properties.

In a further aspect of the present invention a method for producing a multifocal lens having several concentric diffractive zones on a surface of the lens is presented, wherein the method includes:

mathematically providing a diffraction phase structure for each diffractive zone by providing for each diffractive zone a piecewise function as defined by equation (1) or a smoothed version of this piecewise function, wherein $\xi$ depends quadratically on a radial distance to the center of the surface of the lens and is normalized with respect to the radial width of the respective diffractive zone and wherein the gradients $p_1$, $p_2$ and $p_3$ are negative, forming the diffractive multifocal lens such that the diffractive zones have the mathematically provided diffraction phase structures.

In another aspect of the present invention a multifocal lens having several concentric diffractive zones on a surface of the lens is presented, which is able to be produced by the method.

It shall be understood that the multifocal lenses of claim 1 and the method for producing a multifocal lens of claim 15 have similar and/or identical preferred embodiments as defined in the dependent claims.

It shall be understood that a preferred embodiment of the invention can also be any combination of the dependent claims with the respective independent claim.

DETAILED DESCRIPTION OF EMBODIMENTS

Figure 1:
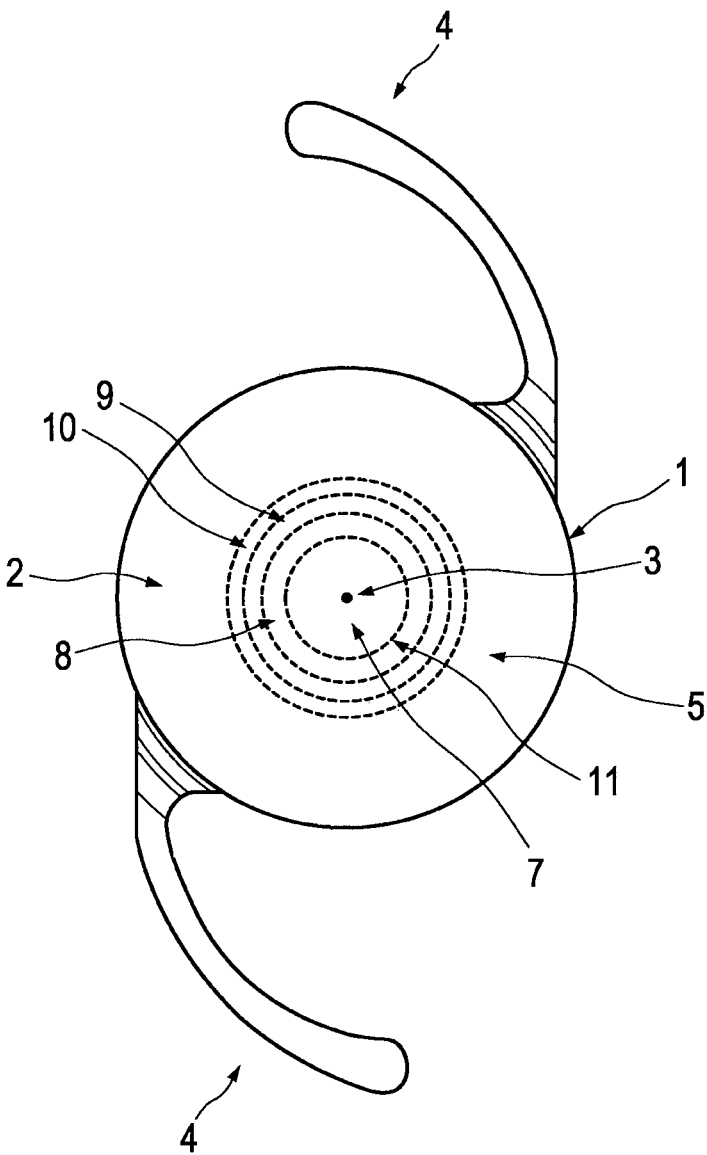
FIG. 1 shows schematically and exemplarily an embodiment of a multifocal lens.

FIG. 1 shows schematically and exemplarily an embodiment of a multifocal lens 1 having several annular diffractive zones 7, 8, 9, 10 on a surface 2. The lens 1 is attached to fixing elements 4 for fixing the lens 1 in an eye, in order to replace a natural lens, which has been removed, by the lens 1. Thus, the lens 1 is an intraocular lens intended to be placed into the capsular bag of the eye after extracapsular cataract removal, functioning as a refractive and diffractive medium to replace the natural crystalline lens of the eye. However, the lens could also be another kind of ocular lens like a contact lens.

In each diffractive zone 7, 8, 9, 10 a respective diffraction phase structure is defined, which is expressible by a piecewise function $\phi(\xi)$ as defined by equation (1) which comprises three phase terms or by a smoothed version of the piecewise function. The surface 2, on which the diffractive zones 7, 8, 9, 10 are provided, is the anterior surface of the lens 1. The diffractive zones 7, 8, 9, 10 extend over a central portion of the anterior surface 2 of the lens 1, wherein in this embodiment four diffractive zones 7, 8, 9, 10 are provided and wherein the radial distance of the outer border of the outermost diffractive zone to the center 3 of the surface 2 is equal to 3.2 mm.

The radial width of the diffractive zones 7, 8, 9, 10 decreases with increasing radial distance of the respective zone 7, 8, 9, 10 to the center 3 of the lens surface 2.

Moreover, the surface 2, on which the several annular diffractive zones 7, 8, 9, 10 are provided, is a refractive surface 2 of the lens 1 such that the outermost diffractive zone is surrounded by a refractive zone 5 which does not comprise a diffractive structure. Thus, the lens surface 2 is a refractive surface, i.e. a curved surface, which provides, together with an opposing second, posterior refractive surface, a base refractive power.

The anterior surface 2 therefore has an inner area with the diffractive zones 7, 8, 9, 10, wherein the inner area provides refractive and diffractive power, and an outer area 5 which surrounds the inner area and which provides refractive power only. The refractive anterior surface 2 is an aspheric lens surface in this embodiment. The posterior surface can also be an aspheric surface or a spheric surface. If the posterior surface is a spheric surface, its radius of curvature can be, for instance, −18.84 mm for a refractive power of 20.0 D. The posterior surface can also be a toric surface, i.e. it can be toroidal in shape to correct astigmatic refractive errors. The sagittal height of a refractive surface having a toroidal shape can be expressed by $$z(x) = \frac{c_x x^2}{1 + \sqrt{1 - c_x^2 x^2}} \text{ and} \tag{4}$$

$$z(y) = \frac{c_y y^2}{1 + \sqrt{1 - c_y^2 y^2}}, \tag{5}$$

wherein x is the distance from the lens center in a first direction being perpendicular to the optical axis of the lens, wherein y is the distance from the lens center in a second direction being perpendicular to the optical axis of the lens and being perpendicular to the first direction, wherein $c_x$ is the curvature, i.e. the reciprocal of the radius of curvature, in the first direction, which might also be named x direction, and wherein $c_y$ is the curvature, in the second direction, which might also be named y direction.

The lens material preferentially comprises an acrylic polymer. It might further comprise an ultraviolet light absorbing agent like benzotriazole and/or a blue-light-filtering chromophore like monomethine. For more details regarding preferred lens materials reference is made to EP 2 375 276 B1 and U.S. Pat. No. 8,556,416 B2.

The smoothed version $\Theta_g(\xi)$ of the function $\phi(\xi)$ is preferentially obtained by convoluting the function $\phi(\xi)$ with a Gaussian kernel, wherein the Gaussian kernel has a standard deviation within a range from 0.02 to 0.04. Preferentially, the standard deviation is 0.03.

Thus, the smoothed version $\Theta_g(\xi)$ might be defined by following equation:

$$\Theta_g(\xi) = \phi(\xi) \otimes g(\xi), \tag{6}$$

wherein $\otimes$ is the convolution operator and $g(\xi)$ is the Gaussian kernel. The convolution operator refers to an integration with the Gaussian kernel in the $L^2$ Hilbert space. The Gaussian kernel is preferentially defined by $$g(\xi) = \frac{1}{\sigma\sqrt{2\pi}} \exp\left(\frac{\xi^2}{2\sigma^2}\right), \tag{7}$$

wherein $\sigma$ is the standard deviation.

The constant $w_1$ is preferentially 0.25 and the constant $w_2$ is preferentially 0.75 such that the radial width of the middle phase term in each diffractive zone 7, 8, 9, 10 is twice the radial width of the inner phase term and hence also twice the radial width of the outer phase term. Moreover, the outer border 11 of at least the innermost diffractive zone 7 is defined by above equation (2), wherein the wavelength A is 546 nm and the add power might be, for instance, 1.75 D.

Generally, phase values can be converted into the sagittal height (sag) of the structure based on a proportional relationship as follows, $$Z(\xi) = \frac{\lambda}{2\pi(n_{IOL} - n_{aqueous})} \phi(\xi), \tag{8}$$

wherein $\lambda/2\pi$ indicates the wave number using the design wavelength of 546 nm, $n_{IOL}$ indicates the refractive index of the lens material and $n_{aqueous}$ indicates the refractive index of the surrounding medium. A sag profile is exemplarily illustrated in FIG. 2 for following set of parameters: $p_1=p_2=-0.8697$, $p_3=-0.3771$, $q_2=0.5352$, $q_3=0.3771$ and $w_1=0.25$, and $w_2=0.75$. The refractive indices can be, for instance, $n_{IOL}=1.544$ and $n_{aqueous}=1.336$.

Figure 2:
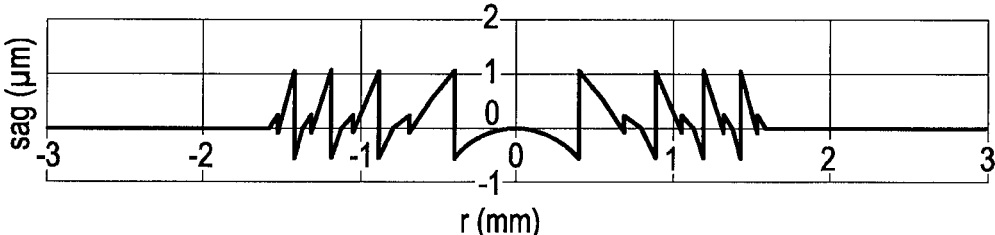
FIG. 2 shows schematically and exemplarily a cross section of a sag profile along a lens diameter.

It should be noted that FIG. 2 just illustrates the result of transforming the diffractive phase profile to the sag profile, wherein the asphericity is not considered. FIG. 2 therefore only illustrates the diffractive profile with no refractive profile superimposed. The aspheric lens surface 2 can be defined by following sag function:

$$S(r) = \frac{cr^2}{1 + \sqrt{1 - (1+k)c^2 r^2}} + \sum_{i=1}^{8} \alpha_i e^{2i}, \tag{9}$$

wherein r denotes the radial distance to the center 3 of the lens surface 2, c denotes the curvature at the center 3 of the lens surface 2, k denotes the conic constant and $\alpha_i$ are the coefficients of the polynomial term up to the sixteenth order. For the lens having a refractive power of, for instance, 20.0 diopters, i.e. 20.0 D, the anterior aspheric surface 2 can be defined by the parameters listed in Table 1, wherein the curvature c might be 1/r or 1/(23 mm) in this example. It should be noted that the values listed in Table 1 are only exemplary values, i.e. the aspheric lens surface can also be defined by other parameters.

TABLE 1

| Optical parameters to form 20.0 D anterior surface of the lens. | |
|---|---|
| Power (D) | 20 |
| Radius (mm) | 23.1 |
| Curvature (mm$^{-1}$) | 0.0433 |
| Conic | −50.05 |
| $a_1$ (mm$^{-1}$) | 6.8102E−4 |
| $a_2$ (mm$^{-3}$) | −1.2892E−3 |
| $a_3$ (mm$^{-5}$) | 8.4459E−4 |
| $a_4$ (mm$^{-7}$) | −2.4020E−4 |
| $a_5$ (mm$^{-9}$) | 3.4589E−5 |
| $a_6$ (mm$^{-11}$) | −2.4960E−6 |
| $a_7$ (mm$^{-13}$) | 7.1633E−08 |
| $a_8$ (mm$^{-15}$) | 0 |

The outer radius of the k-th zone is $r_k$ and the radial extent is $r_{k-1} \leq r \leq r_k$, where $k \in \mathbb{N}$: k=1 ... N is the zone number and N is the number of diffractive zones with N=4 in the present case. The phase of each zone is specified by equation (1), and the relative radial position $\xi_k$, where $0 \leq \xi_k \leq 1$, for the k-th zone is given by following equation:

$$\xi_k = \frac{r^2 - r_{k-1}^2}{r_k^2 - r_{k-1}^2}. \tag{10}$$

The relative radial position is generally defined such that, in the k-th zone, $\xi = \xi_k$.

Taking into account that preferentially $r_0=0$, the relative radial positions for the diffractive zones can be expressed by relations listed in Table 2.

TABLE 2

| Relative radial positions of diffractive zones. | |
|---|---|
| Zone 1 | $\xi_1 = \dfrac{r^2}{r_1^2}$ |
| Zone 2 | $\xi_2 = \dfrac{(r^2 - r_1^2)}{(r_2^2 - r_1^2)}$ |

TABLE 2-continued

| Relative radial positions of diffractive zones. |
| --- |

| Zone 3 | $\xi_3 = \dfrac{(r^2 - r_2^2)}{(r_3^2 - r_2^2)}$ |
| Zone 4 | $\xi_4 = \dfrac{(r^2 - r_3^2)}{(r_4^2 - r_3^2)}$ |

The lens 1 is preferentially a trifocal lens with diffractive orders 0, +1 and +2. In the following corresponding lenses of the far dominant lens type will be described.

The lenses of the far dominant lens type have positive constants $q_2$ and $q_3$ and the parameters of the function $\phi(\xi)$ are the same for all diffractive zones 7, 8, 9, 10. Furthermore, the gradient $p_1$ is within a range from −1.1 to −1.0, the gradient $p_2$ is within a range from −1.1 to −1.0, the gradient $p_3$ is within a range from −1.1 to −1.0, the constant $q_2$ is within a range from 0.3 to 0.4 and the constant $q_3$ is within a range from 1.0 to 1.1. In particular, these parameters can be as defined in Table 3.

TABLE 3

| Parameters of far dominant lens type. | | | | |
| --- | --- | --- | --- | --- |
| Power (D) | $p_1$ | $p_2$ | $p_3$ | $q_2$ | $q_3$ |
| 10.0-15.0 | −1.0973 | −1.0463 | −1.0973 | 0.37415 | 1.0973 |
| 15.5-22.5 | −1.0973 | −1.0158 | −1.0973 | 0.3667 | 1.0973 |
| 23.0-30.0 | −1.0973 | −1.0282 | −1.0973 | 0.3768 | 1.0973 |

In Table 3 three examples of the far dominant lens type for three different respective power ranges are illustrated. In these three examples the constant $w_1$ is 0.25 and the constant $w_2$ is 0.75. Moreover, in these examples the respective outer border for each of the four diffractive zones 7, 8, 9, 10 is defined by equation (2).

Figure 3:
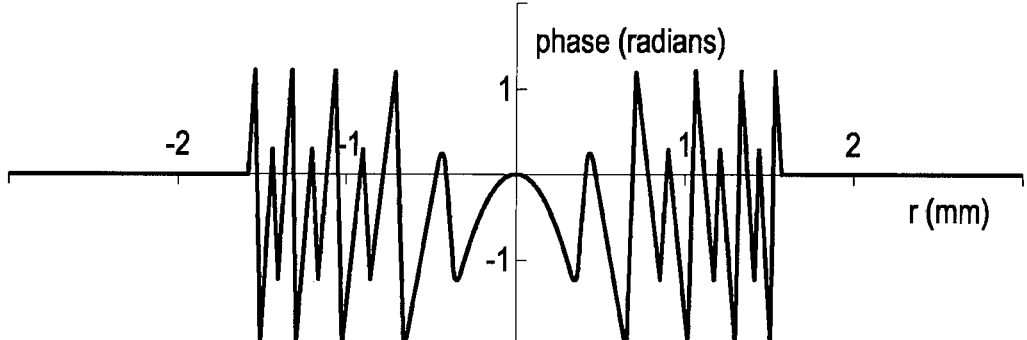
FIG. 3 shows schematically and exemplarily a cross section of a phase profile along a lens diameter of a lens of the far dominant lens type.

FIG. 3 schematically and exemplarily illustrates a phase profile of a lens from the far dominant lens type along the lens diameter.

The lenses of the far dominant lens type are hybrid refractive-diffractive multifocal intraocular lenses (MIOL) that preferentially combine (i) a truncated diffractive profile to produce positive diffraction orders 0, +1, +2 for trifocality and (ii) aspheric optics to improve overall imaging performance. The positive orders of diffraction allow to minimize chromatic aberration of the patient eye, thus mitigating the potential risk of chromatic visual disturbances. The aspheric optics, in turn, reduce the sensitivity of the patient eye to potential decentrations.

Figure 4:
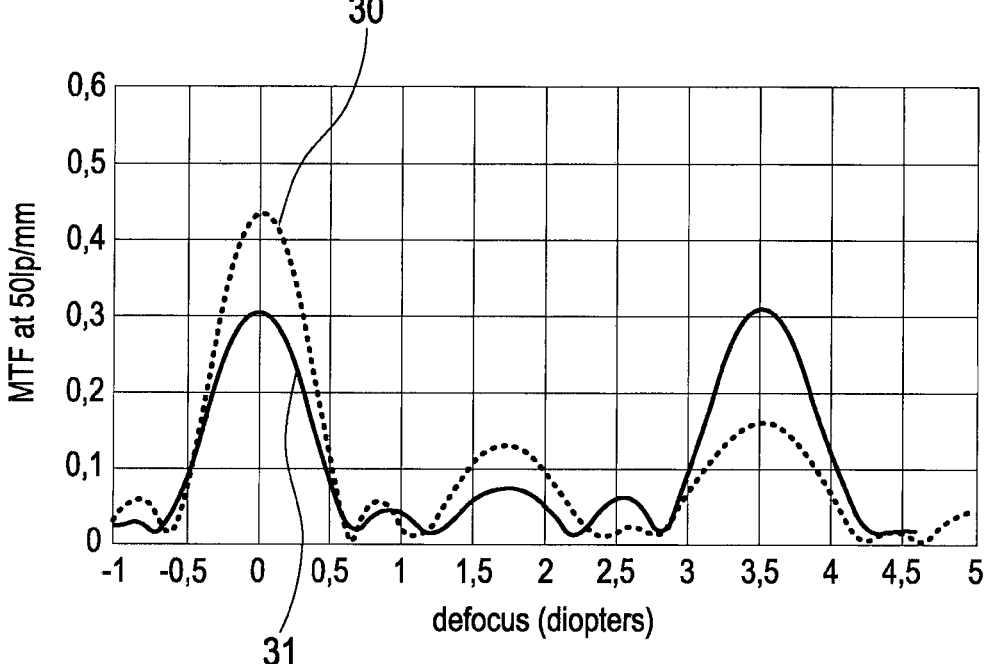
FIG. 4 shows schematically and exemplarily through-focus contrast responses for lenses of the near dominant and far dominant lens types.

In FIG. 4 the graph 30 illustrates a simulated through-focus response (TFR) at a spatial frequency of 50 lp/mm for a lens of the far dominant lens type. The graph 30 is the result of a theoretical evaluation in terms of a modulation transfer function (MTF), wherein, for the simplicity of analysis, a non-toric MIOL is assumed. It is noted that the graph 30 is just used for illustrating the possible relative efficiencies of the different diffractive orders of a lens of the far dominant lens type.

As can be seen in FIG. 4, a lens of the far dominant lens type can provide relatively high far-focus and intermediate-focus contrast levels and an acceptably high near-focus contrast. Such TFR facilitates higher visual acuity at far-focus distances and provides sufficient visual acuities at intermediate and near foci.

In the following lenses of the near dominant lens type will be described.

The lenses of the near dominant lens type have positive constants $q_2$ and $q_3$, the parameters of the function $\phi(\xi)$ can be the same for all diffractive zones 7, 8, 9, 10, and the outer borders of the four diffractive zones 7, 8, 9, 10 are also defined by equation (2). Moreover, the gradient $p_1$ is within a range from −1.2 to −1.0, the gradient $p_2$ is within a range from −1.3 to −1.2, the gradient $p_3$ is within a range from −1.2 to −1.0, the constant $q_2$ is within a range from 0.7 to 0.8 and the constant $q_3$ is within a range from 1.0 to 1.2. It is also possible that, for a lens of the near dominant lens type, the gradients $p_1$, $p_2$ and $p_3$ and the constants $q_2$ and $q_3$ are not the same for all diffractive zones, wherein still preferentially the outer borders of the four diffractive zones 7, 8, 9, 10 are defined by equation (2). In particular, these parameters can be as defined in Table 4.

TABLE 4

| Parameters for near dominant lens type. | | | | | |
| --- | --- | --- | --- | --- | --- |
| Power (D) | $p_1$ | $p_2$ | $p_3$ | $q_2$ | $q_3$ |
| 1st diffractive zone (7) | | | | | |
| 10.0-15.0 | −1.127 | −1.2765 | −1.127 | 0.79395 | 1.127 |
| 15.5-30.0 | −1.0973 | −1.2429 | −1.0973 | 0.77305 | 1.0973 |
| 2nd and 4th diffractive zones (8, 9, 10) | | | | | |
| 10.0-15.0 | −1.0973 | −1.2429 | −1.0973 | 0.77305 | 1.0973 |
| 15.5-30.0 | −1.0973 | −1.2429 | −1.0973 | 0.77305 | 1.0973 |

In Table 4 two examples of the near dominant lens type for two different respective power ranges are illustrated. Also in these examples the constant $w_1$ is 0.25 and the constant $w_2$ is 0.75. Moreover, with respect to the 10.0 D-15.0 D example of the near dominant lens type, the gradients $p_1$, $p_2$ and $p_3$, and the constants $q_2$ and $q_3$ are not the same for all diffractive zones 7, 8, 9, 10. In particular, the gradients $p_1$, $p_2$ and $p_3$, and the constants $q_2$ and $q_3$ of the innermost diffractive zone 7 differ from the gradients $p_1$, $p_2$ and $p_3$, and the constants $q_2$ and $q_3$ of the other diffractive zones 8, 9, 10, wherein the gradients $p_1$, $p_2$ and $p_3$, and the constants $q_2$ and $q_3$ for all other diffractive zones 8, 9, 10 are the same. For the 15.0 D-30.0 D example of the near dominant lens type the gradients $p_1$, $p_2$ and $p_3$, and the constants $q_2$ and $q_3$ are the same for all diffractive zones 7, 8, 9, 10.

Figure 5:
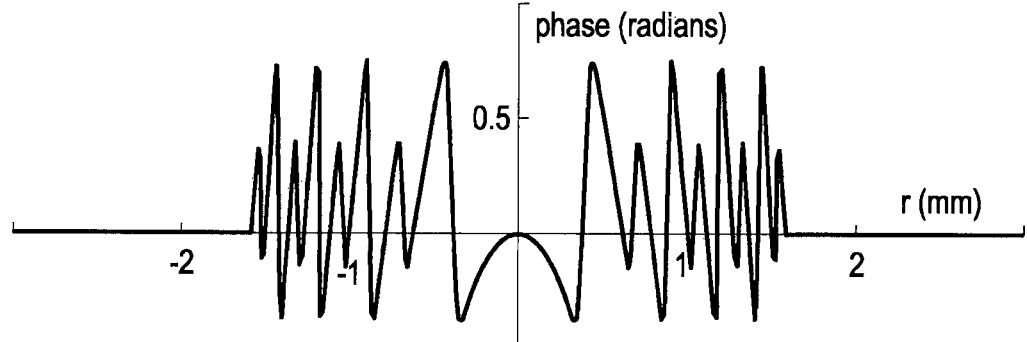
FIG. 5 shows schematically and exemplarily a cross section of a phase profile along a lens diameter of a lens of the near dominant lens type.
Figure 6:
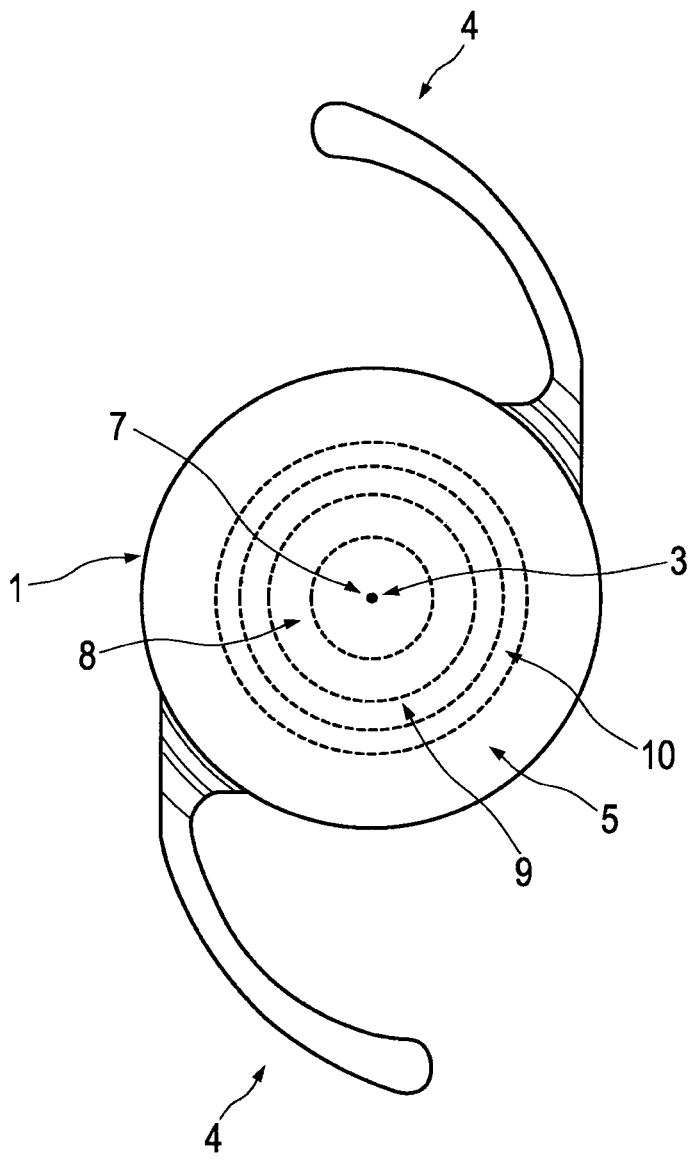
FIG. 6 shows schematically and exemplarily an embodiment of a multifocal lens.

FIG. 5 schematically and exemplarily illustrates a phase profile of a lens from the near dominant type along the lens diameter.

Also the lenses of the near dominant lens type are hybrid refractive-diffractive lenses that combine (i) a truncated diffractive profile to produce positive diffraction orders 0, +1, +2 for trifocality and (ii) an aspheric optics to improve overall imaging performance. As mentioned above, the positive orders of diffraction allow to minimize chromatic aberration of the patient eye, thus, mitigating the potential risk of chromatic visual disturbances. The aspheric optics, in turn, reduces the sensitivity of the patient eye to potential decentrations.

FIG. 4 also shows a graph 31 which illustrates a TFR at a spatial frequency of 50 lp/mm for a lens of the near dominant lens type. Also with respect to the near dominant lens type it is noted that FIG. 4 is just used for illustrating possible relative efficiencies of the different diffractive orders of a lens. As can be seen in FIG. 4, as compared to the contrast response 30 of the lens of the far dominant lens type, the response 31, i.e. the graph 31, of the lens of the near dominant lens type provides lower far-focus and intermediate-focus contrast levels, wherein the near-focus contrast is noticeably higher. Such TFR facilitates near-focus visual acuity and provides sufficient visual acuities at intermediate and near foci.

Figure 7:
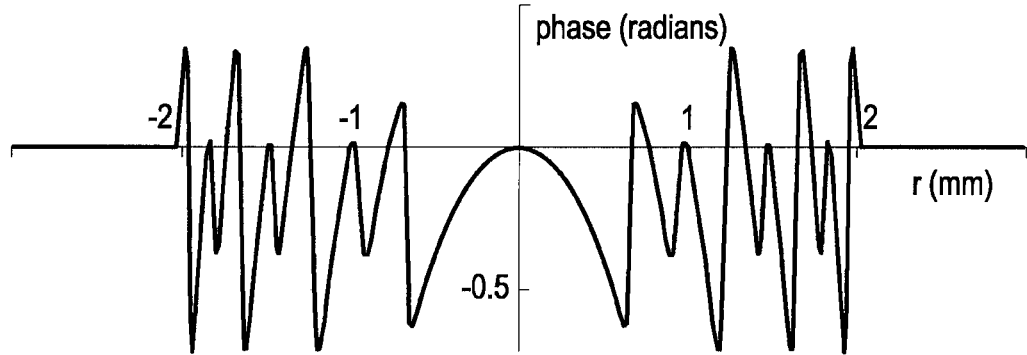
FIG. 7 shows schematically and exemplarily a cross section of a phase profile along the lens diameter for a lens of the intermediate vision lens type.

The diffractive zones of the lenses of the far dominant lens type and the near dominant lens type might cover a relatively small inner area having a radius perpendicular to the optical axis being 3.2 mm. This is indicated in FIG. 1. In the following lenses of the intermediate vision lens type will be described, wherein the diffractive zones 7, 8, 9, 10 might cover a larger area having a radius perpendicular to the optical axis being 4.0 mm. This is indicated in FIG. 7.

With respect to the lenses of the intermediate vision lens type, only the outer border of the innermost diffractive zone 7 is defined by equation (2), whereas the outer border of the other diffractive zones 8, 9, 10 is defined by equation (3). Also for the intermediate vision lens type the constant $w_1$ is preferentially 0.25 and $w_2$ is preferentially 0.75. Furthermore, the gradients $p_1$, $p_2$ and $p_3$, and the constants $q_2$ and $q_3$ are not the same for all diffractive zones 7, 8, 9, 10. In particular, the gradients $p_1$, $p_2$ and $p_3$, and the constants $q_2$ and $q_3$ are different for all diffractive zones 7, 8, 9, 10. Thus, there are not two diffractive zones having the same parameters $p_1$, $p_2$, $p_3$, $q_2$ and $q_3$. Moreover, for the intermediate vision lens type, the gradient $p_1$ is within a range from $-1.2$ to $-0.4$, the gradient $p_2$ is within a range from $-1.0$ to $-0.1$, the gradient $p_3$ is within a range from $-1.2$ to $-0.4$, the constant $q_2$ is within a range from $-0.2$ to 0.3 and the constant $q_3$ is within a range from 0.4 to 1.2. Exemplary values are given in Table 5.

TABLE 5

| Parameters for intermediate vision lens type. | | | | | |
|---|---|---|---|---|---|
| Power (D) | $p_1$ | $p_2$ | $p_3$ | $q_2$ | $q_3$ |
| $1^{st}$ diffractive zone (7) | | | | | |
| 10.0-15.0 | −0.501 | −0.501 | −0.501 | 0.0006 | 0.501 |
| 15.5-22.5 | −0.467 | −0.467 | −0.467 | −0.0033 | 0.467 |
| 23.0-30.0 | −0.501 | −0.501 | −0.501 | 0.0006 | 0.501 |
| $2^{nd}$-$4^{th}$ diffractive zones (8, 9, 10) | | | | | |
| 10.0-15.0 | −0.9239 | −0.926 | −0.9239 | 0.2924 | 0.9239 |
| 15.5-22.5 | −1.14 | −0.1399 | −1.14 | −0.11325 | 1.14 |
| 23.0-30.0 | −0.9239 | −0.926 | −0.9239 | 0.2924 | 0.9239 |

In Table 5 three examples of the intermediate vision lens type for three different respective power ranges are illustrated.

Figure 8:
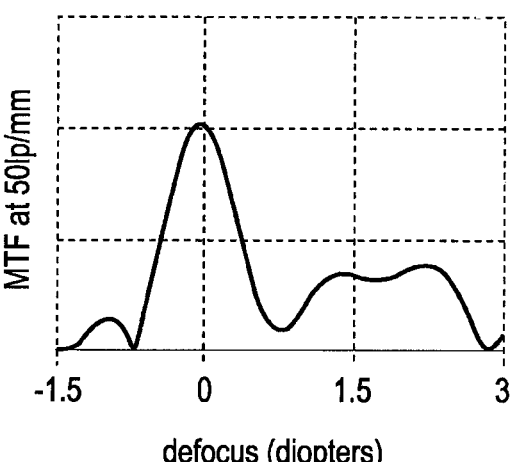
FIG. 8 shows schematically and exemplarily a through-focus contrast response for a lens of the intermediate vision lens type.

FIG. 7 schematically and exemplarily illustrates a phase profile of a lens of the intermediate vision lens type along the lens diameter. FIG. 8 illustrates a TFR at a spatial frequency of 50 lp/mm of a lens of the intermediate vision lens type. The lenses of the intermediate vision lens type are preferentially presbyopic-correction multifocal intraocular lenses with a relatively low addition power. They preferentially target to provide functional vision from distance to intermediate viewing range.

For the lenses of the intermediate vision lens type the radius $r_1$ of the first annular zone, i.e. the outer border of the first annular zone 7, is preferentially given in accordance with equation (2) by $$r_1 = \sqrt{\frac{2\lambda}{p} + \lambda^2},\tag{11}$$

where A is the design wavelength, i.e. k=546 nm in the present case, and p is the add power for +1 diffractive order, wherein preferentially p=2.0 D for intermediate vision lenses.

The radius $r_k$ of the surrounding zones from the second to the fourth diffractive zones 8, 9, 10 is given by, for example $$\sqrt{f^2 + r_k^2} - \sqrt{f^2 + r_{k-1}^2} = \lambda, k = 2, 3, 4,\tag{12}$$

wherein f indicates a focal length. Equation (12) is applied for annular zones from the second to the fourth, based on such consideration that the rays propagating towards the on-axis focus from adjacent zones generate a path difference of one wavelength.

Following equation (13) is an analytical solution of equation (12):

$$r_k = \left(r_{k-1}^2 + \lambda^2 + \sqrt{\frac{4\lambda^2}{p^2} + 4\lambda^2 r_{k-1}^2}\right)^{1/2}, k = 2, 3, 4,\tag{13}$$

where $\lambda$ is the design wavelength, i.e. preferentially 546 nm, and p is the add power for the +1 diffractive order, wherein preferentially p=1.0 D for intermediate vision lenses.

Thus, in an embodiment, for lenses of the intermediate vision lens type, the first central zone (k=1) is formed by using add power p=2.0 D, corresponding to the second diffractive order, and the surrounding zones (k=2,3,4) are formed by using p=1.0 D, corresponding to the first diffractive order.

With the assumption that the higher order terms of $\lambda$ are negligible, an approximate relationship to derive radii $r_k$ based on $r_{k-1}$ becomes $$r_k = \sqrt{\frac{2\lambda}{P} + r_{k-1}^2}, k = 2, 3, 4.\tag{14}$$

Equations (11) to (14) can be used to calculate the radii of the diffractive zones for the intermediate vision lens type lenses.

Figure 9:
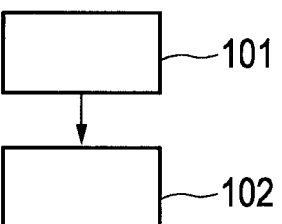
FIG. 9 shows a flowchart exemplarily illustrating an embodiment of a method for producing a multifocal lens having several annular diffractive zones on a surface of the lens.

In the following an embodiment of a method for producing a multifocal lens having several annular diffractive zones on a surface of the lens will exemplarily be described with reference to a flowchart shown in FIG. 9.

In step 101 a diffraction phase structure for each diffractive zone 7, 8, 9, 10 is mathematically provided by providing for each diffractive zone 7, 8, 9, 10 the piecewise function (1). In step 102 the diffractive multifocal lens is formed such that the diffractive zones 7, 8, 9, 10 have the mathematically provided diffraction phase structures. The lens might be formed, for instance, by using a known molding procedure and a known lathe cutting procedure, or by another technique generally used for manufacturing lenses.

Although in above described embodiments the lenses have certain parameters of the function $\phi(\xi)$, the lenses could also have other parameters, as long as depends quadratically on the radial distance to the center of the surface of the lens and is normalized with respect to the radial width of the respective diffractive zone and the gradients $p_1$, $p_2$ and $p_3$ are negative.

As mentioned above, the values listed in Table 1 are only exemplary values, i.e. the aspheric lens surface can also be defined by other parameters. For instance, for a lens having a refractive power of, for instance, 20.0 D the anterior aspheric surface 2 can be defined by the parameters listed in following Table 6, wherein the curvature c might be 1/r or 1/(23 mm) in this example.

TABLE 6

Optical parameters to form 20.0 D anterior surface of the lens.

| Power (D) | 20 |
| --- | --- |
| Radius (mm) | 23.1 |
| Curvature (mm$^{-1}$) | 0.0433 |
| Conic | −48.89 |
| $a_1$ (mm$^{-1}$) | −7.0541E-3 |
| $a_2$ (mm$^{-3}$) | −1.1978E-3 |
| $a_3$ (mm$^{-5}$) | 8.5233E-4 |
| $a_4$ (mm$^{-7}$) | −2.5816E-4 |
| $a_5$ (mm$^{-9}$) | 3.8855E-5 |
| $a_6$ (mm$^{-11}$) | −2.8956E-6 |
| $a_7$ (mm$^{-13}$) | 8.5155E-08 |
| $a_8$ (mm$^{-15}$) | 0 |

Although the parameters listed in above Tables 3 to 5 have a certain accuracy, i.e. a certain number of decimal places, the accuracy can also be different. In a preferred embodiment, the accuracy of the parameters $p_1$, $p_2$, $p_3$, $q_2$ and $q_3$ is given by three decimal places. Thus, the parameters can be as listed in following Tables 7 to 9.

TABLE 7

Parameters of far dominant lens type.

| Power (D) | $p_1$ | $p_2$ | $p_3$ | $q_2$ | $q_3$ |
| --- | --- | --- | --- | --- | --- |
| 10.0-15.0 | −1.097 | −1.046 | −1.097 | 0.374 | 1.097 |
| 15.5-22.5 | −1.097 | −1.016 | −1.097 | 0.367 | 1.097 |
| 23.0-30.0 | −1.097 | −1.028 | −1.097 | 0.377 | 1.097 |

In Table 7 the three examples of the far dominant lens type for three different respective power ranges are illustrated, wherein, in comparison to Table 3, the number of decimal places for all parameters $p_1$, $p_2$, $p_3$, $q_2$ and $q_3$ is three. As mentioned above with respect to Table 3, in these three examples the constant $w_1$ is 0.25 and the constant $w_2$ is 0.75. Moreover, in these examples the respective outer border for each of the four diffractive zones 7, 8, 9, 10 is defined by equation (2).

14

TABLE 8

Parameters for near dominant lens type.

| Power (D) | $p_1$ | $p_2$ | $p_3$ | $q_2$ | $q_3$ |
| --- | --- | --- | --- | --- | --- |
| 1st diffractive zone (7) | | | | | |
| 10.0-15.0 | −1.127 | −1.277 | −1.127 | 0.794 | 1.127 |
| 15.5-30.0 | −1.097 | −1.243 | −1.097 | 0.773 | 1.097 |
| 2nd and 4th diffractive zones (8, 9, 10) | | | | | |
| 10.0-15.0 | −1.097 | −1.243 | −1.097 | 0.773 | 1.097 |
| 15.5-30.0 | −1.097 | −1.243 | −1.097 | 0.773 | 1.097 |

In Table 8 the two examples of the near dominant lens type for two different respective power ranges are illustrated, wherein, in comparison to Table 4, the number of decimal places for all parameters $p_1$, $p_2$, $p_3$, $q_2$ and $q_3$ is three. Also in these examples the constant $w_1$ is 0.25 and the constant $w_2$ is 0.75. Moreover, with respect to the 10.0 D-15.0 D example of the near dominant lens type, the parameters $p_1$, $p_2$ and $p_3$, and the parameters $q_2$ and $q_3$ are not the same for all diffractive zones 7, 8, 9, 10. In particular, the parameters $p_1$, $p_2$ and $p_3$, and the parameters $q_2$ and $q_3$ of the innermost diffractive zone 7 differ from the parameters $p_1$, $p_2$ and $p_3$, and the parameters $q_2$ and $q_3$ of the other diffractive zones 8, 9, 10, wherein the parameters $p_1$, $p_2$ and $p_3$, and the parameters $q_2$ and $q_3$ for all other diffractive zones 8, 9, 10 are the same. For the 15.0 D-30.0 D example of the near dominant lens type the parameters $p_1$, $p_2$ and $p_3$, and the parameters $q_2$ and $q_3$ are the same for all diffractive zones 7, 8, 9, 10.

TABLE 9

Parameters for intermediate vision lens type.

| Power (D) | $p_1$ | $p_2$ | $p_3$ | $q_2$ | $q_3$ |
| --- | --- | --- | --- | --- | --- |
| $1^{st}$ diffractive zone (7) | | | | | |
| 10.0-15.0 | −0.501 | −0.501 | −0.501 | 0.001 | 0.501 |
| 15.5-22.5 | −0.467 | −0.467 | −0.467 | −0.003 | 0.467 |
| 23.0-30.0 | −0.501 | −0.501 | −0.501 | 0.001 | 0.501 |
| $2^{nd}$-$4^{th}$ diffractive zones (8, 9, 10) | | | | | |
| 10.0-15.0 | −0.924 | −0.926 | −0.924 | 0.292 | 0.922 |
| 15.5-22.5 | −1.140 | −0.140 | −1.140 | −0.113 | 1.140 |
| 23.0-30.0 | −0.924 | −0.926 | −0.924 | 0.292 | 0.924 |

In Table 9 three examples of the intermediate vision lens type for three different respective power ranges are illustrated, wherein, in comparison to Table 5, the number of decimal places for all parameters $p_1$, $p_2$, $p_3$, $q_2$ and $q_3$ is three.

Although in above described embodiments the diffractive zones are provided on the anterior surface and not on the posterior surface, they could also be provided on the posterior surface and not on the anterior surface, or on both surfaces.

Although in above described embodiments the lens is an intraocular lens, the lens can also be another kind of ocular lens like a contact lens.

Although in above described embodiments the number of the diffractive zones is four, the number of diffractive zones can also be different. For instance, the number of diffractive zones can be two, three or larger than four. Preferentially, the number of diffractive zones is 13 or smaller, but not larger than 13. Correspondingly, preferentially, in equations (12) to (14), if k=2, . . . , $k_{max}$, $k_{max}$ is maximally 13.

Although in above described embodiments a Gaussian smoothing is used, it is also possible to use another kind of smoothing like a smoothing procedure utilizing a parabolic curve.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

Any reference signs in the claims should not be construed as limiting the scope.

The invention claimed is:

1. A multifocal lens (1) having several concentric diffractive zones L 8, 9, 10) on a surface (2) of the lens, wherein in each diffractive zone (7, 8, 9, 10) a diffraction phase structure is defined, which diffraction phase structure is expressible by the following piecewise function, which comprises three phase terms:

$$\phi(\xi) = 2\pi \times \begin{cases} p_1\xi, & 0 \le \xi < w_1 \\ p_2\xi + q_2, & w_1 \le \xi < w_2, \\ p_3\xi + q_3, & w_2 \le \xi < 1 \end{cases}$$

wherein $\xi$ indicates a position within the respective diffractive zone (7, 8, 9, 10) in a radial direction, $\phi(\xi)$ indicates a phase shift experienced by light passing through the position indicated by $\xi$, $w_1$ and $w_2$ define a spatial partitioning of the respective diffractive zone (7, 8, 9, 10) in the radial direction in accordance with the three phase terms, $p_1$, $p_2$ and $p_3$ indicate gradients of the three phase terms and $q_2$ and $q_3$ are constants, wherein $\xi$ depends quadratically on a radial distance to the center of the surface (2) of the lens (1) and is normalized with respect to the radial width of the respective diffractive zone (7, 8, 9, 10), and wherein the gradients $p_1$, $p_2$ and $p_3$ are negative.

2. The multifocal lens as defined by claim 1, wherein the lens (1) is a trifocal lens with diffractive orders 0, +1 and +2.

3. The multifocal lens as defined by claim 2, wherein the constants $q_2$ and $q_3$ are positive.

4. The multifocal lens as defined by claim 2, wherein the gradient p is within a range from −1.2 to −0.4, the gradient $p_2$ is within a range from −1.0 to −0.1, the gradient $p_3$ is within a range from −1.2 to −0.4, the constant $q_2$ is within a range from −0.2 to 0.3 and the constant $q_3$ is within a range from 0.4 to 1.2.

5. The multifocal lens as defined by claim 1, wherein the constants $q_2$ and $q_3$ are positive.

6. The multifocal lens as defined by claim 5, wherein the gradient $p_1$ is within a range from −1.1 to −1.0, the gradient $p_2$ is within a range from −1.1 to −1.0, the gradient $p_3$ is within a range from −1.1 to −1.0, the constant $q_2$ is within a range from 0.3 to 0.4 and the constant $q_3$ is within a range from 1.0 to 1.1.

7. The multifocal lens as defined by claim 5, wherein the gradient $p_1$ is within a range from −1.2 to −1.0, the gradient $p_2$ is within a range from −1.3 to −1.2, the gradient $p_3$ is within a range from −1.2 to −1.0, the constant $q_2$ is within a range from 0.7 to 0.8 and the constant $q_3$ is within a range from 1.0 to 1.2.

8. The multifocal lens as defined by claim 1, wherein the gradient $p_1$ is within a range from −1.2 to −0.4, the gradient $p_2$ is within a range from −1.0 to −0.1, the gradient $p_3$ is within a range from −1.2 to −0.4, the constant $q_2$ is within a range from −0.2 to 0.3 and the constant $q_3$ is within a range from 0.4 to 1.2.

9. The multifocal lens as defined by claim 1, wherein the constant $w_1$ is 0.25 and the constant $w_2$ is 0.75 such that the radial width of the middle phase term is twice the radial width of the inner phase term.

10. The multifocal lens as defined by claim 1, wherein the outer border (11) of at least the innermost diffractive zone (7) is defined by $$r_k = \sqrt{\frac{2\lambda k}{p} + k^2\lambda^2},$$

wherein k indicates the respective diffractive zone, $\lambda$ is the wavelength of the light and p is a predefined value defining an add power.

11. The multifocal lens as defined by claim 10, wherein the equation of claim 9 defines the outer border of the innermost diffractive zone (7) and the outer border of the other diffractive zones (8, 9, 10) is defined by $$r_k \left( r_{k-1}^2 + \lambda^2 + \sqrt{\frac{4\lambda^2}{p^2} + 4\lambda^2 r_{k-1}^2} \right)^{1/2}.$$

12. The multifocal lens as defined by claim 1, wherein the constants $w_1$ and $w_2$ are the same for all diffractive zones (7, 8, 9, 10).

13. The multifocal lens as defined by claim 1, wherein the gradients $p_1$, $p_2$ and $p_3$, and the constants $q_2$ and $q_3$ are the same for all diffractive zones (7, 8, 9, 10).

14. The multifocal lens as defined by claim 1, wherein the gradients $p_1$, $p_2$ and $p_3$, and the constants $q_2$ and $q_3$ are not the same for all diffractive zones (7, 8, 9, 10).

15. The multifocal lens as defined by claim 1, wherein the gradients $p_1$, $p_2$ and $p_3$, and the constants $q_2$ and $q_3$ are different for all diffractive zones (7, 8, 9, 10).

16. A method for producing a multifocal lens (1) having several concentric diffractive zones (7, 8, 9, 10) on a surface (2) of the lens, wherein the method comprises:

mathematically providing a diffraction phase structure for each diffractive zone (7, 8, 9, 10) by providing for each diffractive zone (7, 8, 9, 10) following piecewise function, which comprises three phase terms:

$$\phi(\xi) = 2\pi \times \begin{cases} p_1\xi, & 0 \le \xi < w_1 \\ p_2\xi + q_2, & w_1 \le \xi < w_2, \\ p_3\xi + q_3, & w_2 \le \xi < 1 \end{cases}$$

wherein $\xi$ indicates a position within the respective diffractive zone (7, 8, 9, 10) in a radial direction, $\phi(\xi)$ indicates a phase shift experienced by light passing through the position indicated by $\xi$, $w_1$ and $w_2$ define a spatial partitioning of the respective diffractive zone (7, 8, 9, 10) in the radial direction in accordance with the three phase terms, $p_1$, $p_2$ and $p_3$ indicate gradients of the three phase terms and $q_2$ and $q_3$ are constants, wherein $\xi$ depends quadratically on a radial distance to the center of the surface (2) of the lens (1) and is normalized with respect to the radial width of the respective diffractive zone (7, 8, 9, 10), and wherein the gradients $p_1$, $p_2$ and $p_3$ are negative; and forming the diffractive multifocal lens (1) such that the diffractive zones (7, 8, 9, 10) have the mathematically provided diffraction phase structures.

17. A multifocal lens (1) having several concentric diffractive zones (7, 8, 9, 10) on a surface (2) of the lens, wherein in each diffractive zone (7, 8, 9, 10) a diffraction phase structure is defined, which diffraction phase structure is expressible by a smoothed version of the following piecewise function, which comprises three phase terms:

$$\phi(\xi) = 2\pi \times \begin{cases} p_1\xi, & 0 \le \xi < w_1 \\ p_2\xi + q_2, & w_1 \le \xi < w_2 \\ p_3\xi + q_3, & w_2 \le \xi < 1 \end{cases},$$

wherein $\xi$ indicates a position within the respective diffractive zone (7, 8, 9, 10) in a radial direction, $\phi(\xi)$ indicates a phase shift experienced by light passing through the position indicated by $\xi$, $w_1$ and $w_2$ define a spatial partitioning of the respective diffractive zone (7, 8, 9, 10) in the radial direction in accordance with the three phase terms, $p_1$, $p_2$ and $p_3$ indicate gradients of the three phase terms and $q_2$ and $q_3$ are constants, wherein $\xi$ depends quadratically on a radial distance to the center of the surface (2) of the lens (1) and is normalized with respect to the radial width of the respective diffractive zone (7, 8, 9, 10), and wherein the gradients $p_1$, $p_2$ and $p_3$ are negative.

18. A method for producing a multifocal lens (1) having several concentric diffractive zones (7, 8, 9, 10) on a surface (2) of the lens, wherein the method comprises:

mathematically providing a diffraction phase structure for each diffractive zone (7, 8, 9, 10) by providing for each diffractive zone (7, 8, 9, 10) a smoothed version of following piecewise function, which comprises three phase terms:

$$\phi(\xi) = 2\pi \times \begin{cases} p_1\xi, & 0 \le \xi < w_1 \\ p_2\xi + q_2, & w_1 \le \xi < w_2 \\ p_3\xi + q_3, & w_2 \le \xi < 1 \end{cases},$$

wherein $\xi$ indicates a position within the respective diffractive zone (7, 8, 9, 10) in a radial direction, $\phi(\xi)$ indicates a phase shift experienced by light passing through the position indicated by $\xi$, $w_1$ and $w_2$ define a spatial partitioning of the respective diffractive zone (7, 8, 9, 10) in the radial direction in accordance with the three phase terms, $p_1$, $p_2$ and $p_3$ indicate gradients of the three phase terms and $q_2$ and $q_3$ are constants, wherein $\xi$ depends quadratically on a radial distance to the center of the surface (2) of the lens (1) and is normalized with respect to the radial width of the respective diffractive zone (7, 8, 9, 10), and wherein the gradients $p_1$, $p_2$ and $p_3$ are negative; and forming the diffractive multifocal lens (1) such that the diffractive zones (7, 8, 9, 10) have the mathematically provided diffraction phase structures.

\* \* \* \* \*